US010545097B2

(12) United States Patent
Fillon et al.

(10) Patent No.: US 10,545,097 B2
(45) Date of Patent: Jan. 28, 2020

(54) DEVICE FOR OPTICALLY INSPECTING GLASS RECEPTACLES AS THEY LEAVE A MOULDING MACHINE

(71) Applicant: TIAMA, Vourles (FR)

(72) Inventors: Pascal Fillon, Grezieu la Varenne (FR); Florent Fougere, l'Arbresle (FR); Adrien Chabert, Lyons (FR)

(73) Assignee: TIAMA, Vourles (FR)

( * ) Notice: Subject to any disclaimer, the term of this patent is extended or adjusted under 35 U.S.C. 154(b) by 0 days.

(21) Appl. No.: 16/333,320

(22) PCT Filed: Sep. 19, 2017

(86) PCT No.: PCT/FR2017/052507
§ 371 (c)(1),
(2) Date: Mar. 14, 2019

(87) PCT Pub. No.: WO2018/051049
PCT Pub. Date: Mar. 22, 2018

(65) Prior Publication Data
US 2019/0250106 A1 Aug. 15, 2019

(30) Foreign Application Priority Data

Sep. 19, 2016 (FR) ...................................... 16 58759

(51) Int. Cl.
*G01N 21/90* (2006.01)
*G01N 21/958* (2006.01)

(52) U.S. Cl.
CPC ....... *G01N 21/9036* (2013.01); *G01N 21/958* (2013.01); *G01N 2021/9063* (2013.01); *G01N 2201/061* (2013.01); *G01N 2201/0634* (2013.01)

(58) Field of Classification Search
CPC ............. G01N 21/9036; G01N 21/958; G01N 2021/9063; G01N 2201/061; G01N 2201/0634
USPC ................................ 356/239.4, 239.7, 240.1
See application file for complete search history.

(56) References Cited

U.S. PATENT DOCUMENTS

| 2008/0291438 A1* | 11/2008 | Akkerman | ............ B07C 5/3404 356/240.1 |
| 2011/0006210 A1* | 1/2011 | Margner | ................ G01N 21/95 250/330 |
| 2018/0136142 A1* | 5/2018 | Will | ....................... G01N 21/90 |

FOREIGN PATENT DOCUMENTS

| DE | 100 17 126 | 6/2001 |
| DE | 10 2014 220598 | 4/2016 |
| EP | 0 177 004 | 4/1986 |
| EP | 1 109 010 | 6/2001 |

(Continued)

*Primary Examiner* — Roy M Punnoose
(74) *Attorney, Agent, or Firm* — Clark & Brody

(57) ABSTRACT

The invention provides a device for optically inspecting high temperature glass containers (2), the device comprising a lighting system (7) having a light-emitting surface that is adapted to emit both: a "flash" first light flux during a flash duration of less than 1 ms and at a wavelength longer than 650 nm; and also a "bottle-scanning" second light flux having wavelengths shorter than 650 nm and for a duration of not less than 2 s, the lighting system (7) being controlled: to emit the flash light flux so that the camera can take images of each container while back-lit by said flash light flux; and to emit the "bottle-scanning" light flux that is perceived by a human eye as being continuous.

14 Claims, 2 Drawing Sheets

(56) References Cited

FOREIGN PATENT DOCUMENTS

FR 2 958 751 10/2011
FR 2 993 662 1/2014

* cited by examiner

DEVICE FOR OPTICALLY INSPECTING GLASS RECEPTACLES AS THEY LEAVE A MOULDING MACHINE

BACKGROUND OF THE INVENTION

The present invention relates to the technical field of optically inspecting translucent or transparent hollow containers or objects that are at high temperature.

The invention relates more particularly to optically inspecting objects such as glass bottles or flasks leaving a manufacturing or forming machine at a high rate.

In conventional manner, a forming machine includes a plurality of cavities, each having a mold in which the container takes on its final shape at high temperature. At the outlet from the forming machine, the containers are moved so as to constitute a row on a transport conveyor causing the containers to pass in succession through various stations for treatments such as spraying and annealing.

It would be advantageous to identify a forming defect at the outlet from the forming machine as soon as possible and before the various treatment stations in order to be able to correct the defect as soon as possible on the forming machine. It is thus advantageous in particular to detect dimensional deviations or deformations of the containers that are associated directly with settings of the forming process, so as to enable the process to be corrected as quickly as possible in the event of any drift.

In the state of the art, it is known to install a contactless optical inspection system at the outlet from the forming machine enabling containers to be inspected while they are still hot, i.e. at a temperature lying in the range 300° C. to 600° C.

For example, patent EP 0 177 004 proposes a system for contactless inspection of still-hot glass containers immediately after they have been formed. That system has a lighting source arranged on one side of the conveyor and a linear camera mounted on the side of the conveyor opposite from its side fitted with the lighting source. The containers move in line between the lighting source and the camera so that they are back-lighted, insofar as the light used for this observation travels from the source to the containers and from the containers to the site of observation.

Independently of that automated inspection system, the operators controlling the forming machine frequently have available a lighting source referred to as a "bottle scanner" that makes it possible to obtain a visual estimate of the quality of the containers leaving the forming machine. The bottle scanner is installed along the conveyor located at the outlet from the forming machine, being situated on the side of the conveyor that is remote from its side where the operators are to be found so that the operators observe the containers while they are back-lit.

Unfortunately, it should be observed that in numerous applications, the space available at the outlet from the forming machine does not leave room for a bottle scanner and an automatic inspection system to be installed.

BRIEF SUMMARY OF THE INVENTION

The present invention seeks to remedy the drawbacks of the prior art by proposing a device for optically inspecting glass containers at high temperature, the device being designed both to enable the containers to be inspected visually by operators and also to enable the containers to be inspected automatically, while also being suitable for being installed at the outlet of the forming machine.

To achieve such an object, the device of the invention provides optical inspection of glass containers at high temperature manufactured in a forming machine, the containers being placed in succession on a conveyor at the outlet from the forming machine to travel at a high rate past the inspection device, which comprises a container lighting system presenting a light-emitting surface, at least one camera taking images of containers back-lighted by the light from the light-emitting surface, and a system for controlling the operation of the lighting system and of the camera.

According to the invention, the light-emitting surface of the lighting system is suitable for emitting both:

a "flash", first light flux for a flash duration shorter than 1 milliseconds (ms) and at a wavelength longer than 650 nanometers (nm); and also a "bottle-scanning", second light flux comprising visible wavelengths shorter than 650 nm and for a duration of not less than 2 seconds (s).

The lighting system is controlled:

to emit the flash light flux for each container travelling past the device in such a manner as to enable the camera to take images of each container back-lighted by said flash light flux; and to emit the "bottle-scanning" light flux independently of the flash light flux, so as to be perceived by a human eye as being continuous.

Furthermore, the system of the invention may also include in combination at least one and/or more of the following additional characteristics:

the system for controlling the lighting system has a manual control for adjusting the intensity of the "bottle-scanning" light flux emitted by the lighting system;

the manual control is a control member mounted on the lighting system or situated remotely from the lighting system;

the lighting system includes a first series of individual light sources for "flash" light that are distributed regularly over the light-emitting surface and that are suitable for producing light at a wavelength in the range 650 nm to 5000 nm;

the lighting system includes a second series of individual light sources for emitting "bottle-scanning" flux that are distributed regularly over the light-emitting surface and that are suitable for producing visible light at wavelengths lying in the range 300 nm to 650 nm;

the individual light sources of the first series and the individual light sources of the second series are positioned in alternating manner on at least one support plate extending in a plane;

the lighting system includes as its light-emitting surface a diffuser placed in front of the support plate for the individual light sources of the first series and for the light sources of the second series;

the lighting system includes a protective pane placed in front of the diffuser;

the lighting system for emitting the flash light flux is controlled by a voltage and/or current and/or pulse duration system to operate at a frequency higher than 50 hertz (Hz);

the lighting system for emitting the flash light flux is controlled by a control system serving to synchronize the passage of containers and the emission of flash light flux and the taking of images by the camera; and the lighting system for emitting the bottle-scanning light flux is controlled by a modulator device operating at a frequency higher than 50 Hz so that the light flux is perceived by a human eye as being continuous.

The invention also provides an inspection device including a conveyor on which high temperature glass containers leaving a forming machine are placed in order to cause them to travel in succession at a high rate past at least one inspection device.

According to the invention, the lighting system for lighting the containers is placed on one side of the conveyor, while the camera is placed on the opposite side of the conveyor in a movement zone for operators.

Furthermore, the installation of the invention may also present in combination at least one and/or more of the following additional characteristics:

the lighting system is provided with a manual control member for adjusting the intensity of the "bottle-scanning" light flux, the control member being mounted on the lighting system so as to be accessible for an operator located in the movement zone and being connected to the system for controlling the lighting system; and the lighting system includes a housing presenting a light-emitting surface on a front face, the housing being fastened to the conveyor.

Various other characteristics appear from the following description made with reference to the accompanying drawings, which show embodiments of the invention as non-limiting examples.

DETAILED DESCRIPTION OF THE INVENTION

Figure 1:
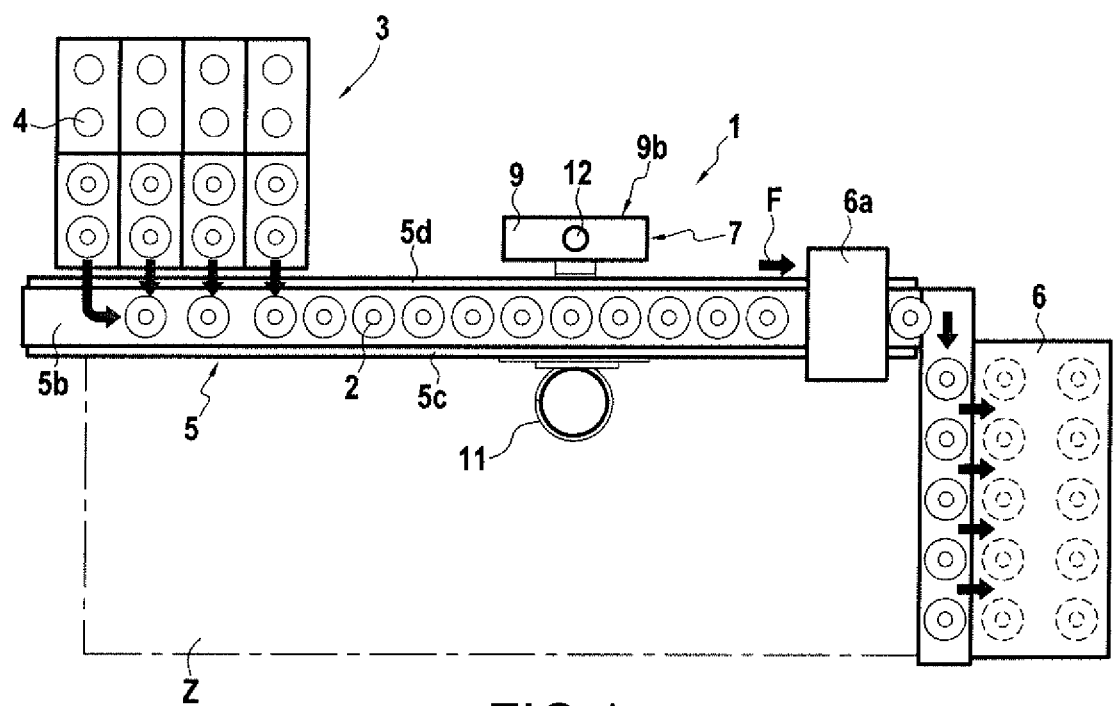
FIG. 1 is a diagrammatic plan view of an inspection device in accordance with the invention positioned at the outlet from a container forming machine.
Figure 2:
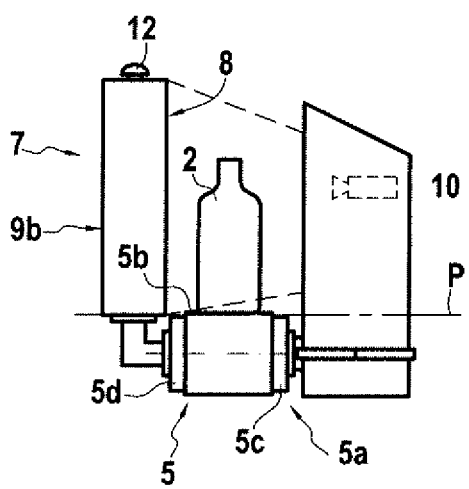
FIG. 2 is a diagrammatic side view showing the inspection device in accordance with the invention as shown in FIG. 1.

As can be seen more clearly in FIG. 1, the invention provides a device 1 for inspecting transparent or translucent containers 2, e.g. such as glass bottles or flasks, while they are hot. The device 1 is placed in such a manner as to be able to inspect the containers 2 leaving a manufacturing or forming machine 3 of any conventionally known type. At the outlet from the forming machine, the containers 2 are at a high temperature, typically lying in the range 300° C. to 600° C.

In conventional manner, the forming machine 3 includes a series of cavities 4, each serving to form a container 2. In known manner, the containers 2 that have just been formed by the machine 3 are placed in succession on an outlet conveyor 5 in order to form a row of containers. The containers 2 are transported in a row by the conveyor 5 in a transfer direction F in order to take them successively to various different treatment stations. Conventionally, the conveyor 5 comprises a stationary structure 5a standing on the floor and supporting a movable belt 5b defining a conveyor plane P on which the containers 2 stand. The conveyor 5 is of height that is variable, i.e. the distance between the conveyor plane P and the floor can be varied, as can the angle of inclination between the transfer direction F and the floor so that the row of containers follows an upward or a downward slope.

The movable belt 5b moves on the stationary structure 5a, which has two side walls 5c and 5d that extend substantially parallel to each other below the conveyor plane P. These two stationary walls 5c and 5d define the two opposite sides of the conveyor 5, i.e. relative to an intervention zone Z in which a person can move, respectively the front side and the rear side of the conveyor. The wall 5c that is thus referred to as the "front" wall defines one side of the intervention zone for a person, while the rear wall of the conveyor is given reference 5d.

In accordance with the invention, the inspection device 1 of the invention is placed as close as possible to the forming machine 3 so that the conveyor 5 causes the containers 2 at high temperature to travel in succession past the inspection device 1, which thus serves to perform in-line inspection of the faulty or non-faulty state of the containers 2. Typically, the device 1 is positioned between the outlet from the forming machine 3 and an annealing oven 6, and preferably before a surface treatment hood Ga that generally constitutes the first of the treatment stations after the forming machine.

The inspection device 1 of the invention has a lighting system 7 for lighting the containers 2 and presenting a light-emitting surface 8 that constitutes the front face of a housing 9. In the embodiment shown, the housing 9 is of rectangular box shape, however it is clear that the housing could be of some other shape. Likewise, the light-emitting surface 8 may be plane or curved. As can be seen in the drawings, the housing 9 has side walls 9a extending perpendicularly relative to a back wall 9b that extends parallel to the light-emitting surface 8, which is rectangular in shape.

The inspection device 1 of the invention also has at least one camera 10 taking images of the containers back-lighted by the light coming from the light-emitting surface 8. For this purpose, the lighting system 7 is positioned on one side of the conveyor 5, while the camera 10 is positioned on the other side of the conveyor 5. The camera 10 is thus positioned on the front side of the conveyor defining the intervention zone Z, while the lighting system 7 is positioned on the rear side of the conveyor 5.

Advantageously, the camera 10 has an objective lens. Typically, the camera 10 comprises an electronic image sensor that delivers a digital or analog electronic image to a system for analyzing and/or storing and/or displaying images. Said image sensor is preferably in the form of an array and a control device serves to control its time (duration) and occurrence (instant) of light integration. It is sensitive to any type of light emitted by the lighting system 7 illuminating the containers. The lens mounted on the camera focuses an optical image of the containers or of a portion of the containers onto the image sensor. In other words, the lens makes an optical image that the image sensor converts into an electronic image. By way of example, the camera 10 is mounted in a mounting box 11.

The box 11 is preferably secured to the conveyor by being mounted directly on the front wall 5c of the conveyor 5. Likewise, the lighting system 8 is secured to the conveyor by being mounted directly on the rear wall 5d of the conveyor 5. The box 11 and the lighting system 8 are secured to the conveyor 5 by any appropriate means for providing a rigid connection with the conveyor.

The inspection device 1 of the invention also has electronic control systems, comprising a system for controlling the lighting system 7 and a system for controlling the camera 10. These control systems (not shown in the figures) are constituted by any electronic means suitable for controlling the operation of the lighting system 7 and of the camera 10. The control system for the light source may optionally be included in the housing 9 of the light source 7. The control systems may be separate or they may be combined in a single piece of equipment. They may also be arranged in and combined with a system for analyzing and/or storing and/or displaying images.

In conventional manner, the control systems are advantageously connected to other members such as the forming system 3 or a coder of the conveyor 5. The system for controlling the camera 10 is suitable for delivering an image integration order to the camera synchronously with the passage of the containers so as to synchronize image acquisition with the passage of a container in the field of observation of the camera. The control system of the light source 7 is suitable for delivering a lighting order to the source synchronously with the passage of the containers and with the interaction performed by the camera in order to enable a container to be illuminated and its image to be acquired at the moment when the container is present in the field of observation of the camera.

In accordance with the invention, the lighting system 7 has a light-emitting surface 8 that is suitable for emitting both a first light flux referred to as a "flash" for a flash duration of less than 1 ms at a wavelength longer than 650 nm, and also a second light flux referred to as a "bottle-scanning" flux that comprises wavelengths shorter than 650 nm and that is emitted for a duration not less than 2 s, and preferably continuously.

It should thus be understood that the light-emitting surface 8 emits a "flash", first light flux at a wavelength longer than 650 nm and typically lying in the range 650 nm to 5000 nm, and advantageously in the range 700 nm to 900 nm, so as to lie outside the visible spectrum. It should be observed that the wavelength of this first light flux is selected so as to be imperceptible to the human eye. Specifically, this flash light flux must not disturb the operators, and must not give rise to them having visual or nervous disorders.

Figure 5:
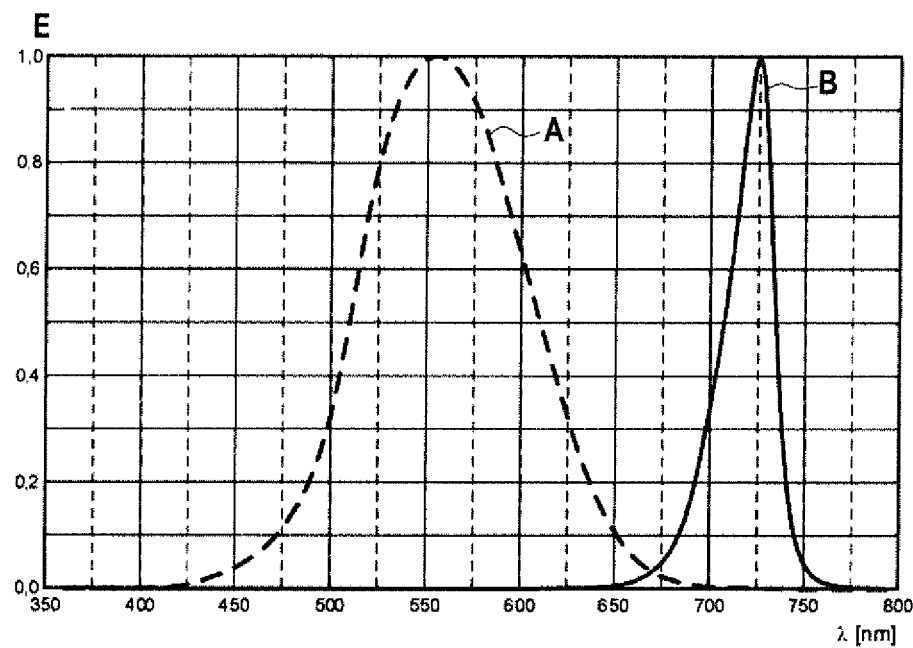
FIG. 5 plots curves A and B of the relative emitted energy E as a function of wavelength λ, respectively for the spectral response of the human eye and for an example spectrum of a "flash" light flux.

Curve A in FIG. 5 shows the spectral response of the human eye, while curve B shows an example spectrum for the flash light flux. It should be observed that the spectrum of the flash light flux is also narrow, having a maximum width of 30 nm at 50% energy.

Furthermore, this "flash" first light flux is emitted for a duration that is as short as possible in order to reduce motion blurring in the images and in order to avoid disturbing an operator. By way of example, the duration of the flash may lie in the range 1 microsecond ($\mu s$) to 1 ms, and advantageously in the range 50 $\mu s$ to 500 $\mu s$. This duration for the first light flux is selected so as to guarantee maximum light intensity at the moment the camera performs inspection. In other words, the lighting system 7 delivers, as the first light flux, infrared pulsed illumination (in the meaning of the Commission Internationale de l'Eclairage (CIE)) that is to be picked up by the camera 10.

Figure 6:
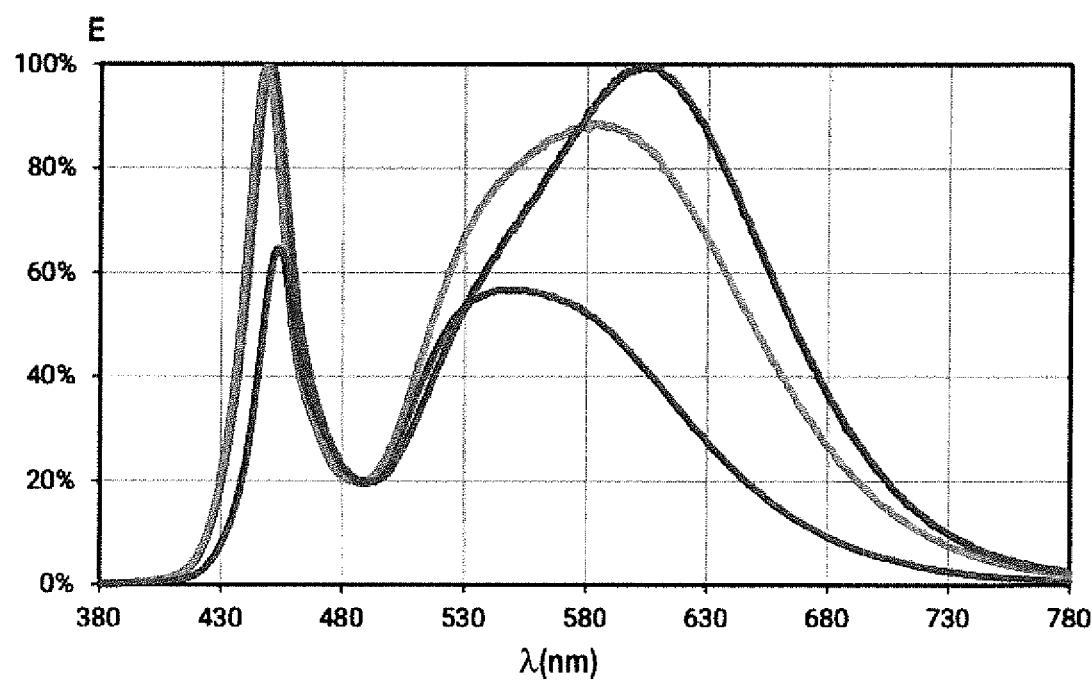
FIG. 6 plots the emitted relative energy E as a function of wavelength λ, showing example spectra for a "bottle-scanning" light flux.

It should be considered that the light-emitting surface 8 also emits a second light flux referred to as the "bottle-scanning" flux, made up of visible wavelengths that are shorter than 650 nm, and that lie typically in the range 300 nm to 650 nm. It should be observed that the wavelength spectrum of this second light flux is selected so as to be perceptible to the human eye and so as to pass through most glass bottles. Typically, the light-emitting surface 8 emits, as the second light flux, light having a broad visible spectrum, e.g. in the form of white light enabling a person situated in the intervention zone Z to inspect the containers by back-lighting. By way of example, FIG. 6 shows examples of spectra for the "bottle-scanning" second light flux.

Furthermore, this "bottle-scanning" second light flux is emitted for a duration longer than 2 ms and advantageously throughout the time a series of containers is going past the inspection device. Typically, this "bottle-scanning" second light flux is emitted continuously throughout the time containers leaving the forming machine are being inspected. Emission is said to be "continuous" when the human eye cannot perceive any significant variation in light intensity. The "bottle-scanning" light flux is thus perceived by a human eye as being continuous. The system for controlling the lighting system 7 is thus suitable for maintaining a light flux in lumens, i.e. perceivable to the human eye, that is stable to within ±5%.

Naturally, between producing two different types of container that leave the same forming machine, the lighting system 7 need no longer deliver this "bottle-scanning" second light flux.

According to another characteristic of the invention, the control system controls the operation of the lighting system 7 so as to emit the flash light flux for each container 2 going past the device in such a manner as to enable the camera 10 to take images for each container back-lit by said flash light flux. The flash light flux is thus emitted while the camera is integrating light.

Thus, as a function of detecting containers 2 going past the inspection device, the control system manages synchronization between the passage of the containers, the emission of flashes of light flux, and the taking of images by the camera, i.e. of integration by the camera. Thus, during the passage of each container 2 between the lighting system 7 and the camera 10, the control systems serve firstly to control the lighting system 7 so that it emits the flash light flux, and secondly to control integration of light by the sensor of the camera 10 so that it takes at least one image of the container while it is back-lit by said flash light flux.

The control system provides voltage and/or current and/or duration control over the lighting system 7 in order to emit the flash light flux.

According to another characteristic of the invention, the control system controls the operation of the lighting system 7 so that it emits the "bottle-scanning" light flux independently of the flash light flux, and maintains it while emitting the flash light flux. In other words, the lighting system 7 is suitable for delivering both white light continuously, and also, on each occasion containers go past the inspection system, infrared pulsed light. Thus, during the passage of each container, the lighting system 7 emits simultaneously the first lighting and the second lighting. The pulsed lighting is added to the continuous lighting.

The control system of the lighting system 7 controls the intensity of the bottle-scanning light flux by modifying the magnitude of a current and/or a voltage.

In a variant of the invention, the control system of the lighting system 7 controls the perceived intensity of the bottle-scanning light flux by using a method of pulse width modulation (PWM). In other words, the perceived light flux is continuous for the eye, but in reality it is made up of successions of pulses of varying width, which are emitted at a modulation frequency that is high enough to give the eye the illusion of continuity. The modulation frequency is higher than 50 Hz and may be as much as 1 kilohertz (kHz). In this variant of the invention, the state of the bottle-scanning light flux while the flash light flux is being emitted may either be maintained, or else be reduced, or indeed be zero, providing the interruption does not lead to discomfort for the human observer insofar as the eye perceives bottle-scanning light flux as being continuous.

According to an advantageous embodiment characteristic, the system for controlling the lighting system includes a manual control 12 for adjusting the intensity of the "bottle-scanning" light flux as emitted by the lighting system. This manual control thus enables the intensity of the light flux to be adapted, in particular as a function of the color and the thickness of the glass of the containers. Advantageously, this manual control 12 can also be used for stopping or starting the emission of the "bottle-scanning" light flux by the lighting system 7.

In a preferred embodiment variant, the manual control 12 is mounted on the lighting system 7. Advantageously, the manual control 12 is mounted on the lighting system 7 so as to be accessible for an operator in the movement zone Z. For example, the manual control 12 may be mounted on the top of the housing 9. The manual control 12 is a control member made in any appropriate manner, such as an electrical dimmer.

In another embodiment variant that is not shown, the manual control 12 is remote from the lighting system 7 so as to be accessible for an operator positioned in the movement zone Z. In this embodiment, the manual control 12 is placed in the movement zone and is connected to the control system for controlling the lighting system 7.

Figure 3:
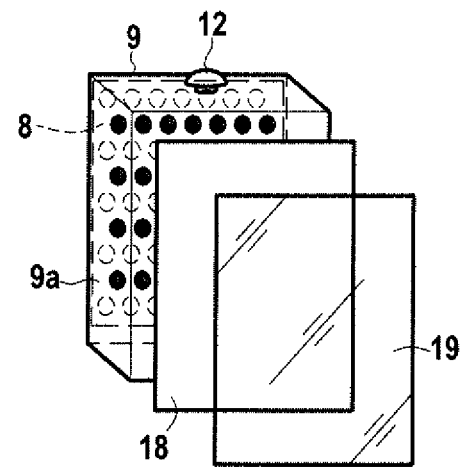
FIG. 3 is a diagrammatic exploded perspective view showing an embodiment of a lighting system in accordance with the invention.
Figure 4:
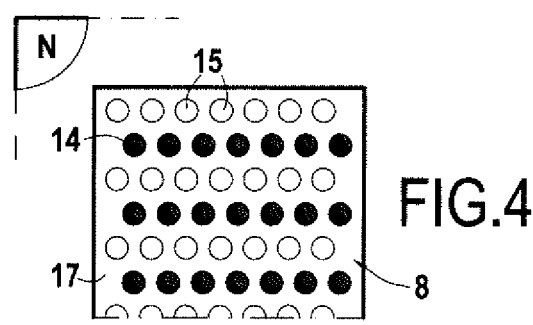
FIG. 4 is a plan view showing a characteristic detail of the lighting system in accordance with the invention.

FIGS. 3 and 4 show a preferred embodiment example of the lighting system 7 in which the light-emitting surface 8 occupies the front face of the housing 9. The light-emitting surface 8 that emits both the "bottle-scanning" light flux and also the flash light flux, presents both a width taken in the travel direction of the containers, and also a height taken perpendicularly to the conveyor plane, that are defined to be greater than the width and height of the traveling containers. The width typically lies in the range 100 millimeters (mm) to 400 mm, and the height lies in the range 200 mm to 800 mm.

The lighting system 7 has a first series of individual light sources 14 for emitting "flash" light that are distributed regularly over the light-emitting surface and that are suitable for producing the first light flux. Typically, the "flash" individual light sources 14 are light-emitting diodes (LEDs or OLEDs).

The lighting system 7 also has a second series of individual light sources 15 for emitting "bottle-scanning" light that are distributed regularly over the light-emitting surface and that are suitable for producing the second light flux. Typically, the "bottle-scanning" individual light sources 15 are light-emitting diodes (LEDs or OLEDs).

The individual light sources 14 of the first series and the individual light sources 15 of the second series are positioned in alternating manner on at least one support plate 17 such as a printed circuit. In the example shown, the light sources 14 and 15 are mounted on a single support plate 17 lying in a plane N. Naturally, the light sources may be mounted on a plurality of superposed support plates 17 that are installed so as to lie in the plane N.

In the example shown in FIG. 4, the individual light sources 14 of the first series are organized in mutually parallel superposed rows, that, by way of example, are also parallel to the transfer direction F. Likewise, the individual light sources 15 of the second series are organized in mutually parallel superposed rows, but they are interleaved between the rows of the first series. Thus, a row of individual light sources of either series lies between two rows of individual light sources of the other series.

In a preferred embodiment shown in FIG. 3, the lighting system 7 includes as its light-emitting surface a diffuser 18 that is arranged in front of the support plate 17 supporting the individual light sources of the first series and the light sources of the second series. The lighting system 7 preferably has a protective pane 19 placed in front of the diffuser 18.

Naturally, if a diffuser 18 is not installed, it should be observed that the light-emitting surface 8 may correspond to the "flash" individual light sources 14 and the "bottle-scanning" light sources 15 taken together. In other words, the light-emitting surface 8 corresponds to a luminous surface from which the emitted light is perceived by the observer or else by the camera.

The invention claimed is:

1. An inspection device for optically inspecting glass containers (2) at high temperature manufactured in a forming machine (3), the containers being placed in succession on a conveyor (5) at the outlet from the forming machine to travel at a high rate past the inspection device (1), which comprises a container lighting system (7) presenting a light-emitting surface (8), at least one camera (10) taking images of containers back-lighted by the light from the light-emitting surface, and a system for controlling the operation of the lighting system (7) and of the camera (10), the inspection device being characterized in that the light-emitting surface (8) of the lighting system (7) is configured for emitting both:
   a "flash" first light flux for a flash duration shorter than 1 ms and at a wavelength longer than 650 nm; and also
   a "bottle-scanning" second light flux comprising visible wavelengths shorter than 650 nm and for a duration of not less than 2 s;
   and in that the lighting system (7) is controlled:
   to emit the flash light flux for each container traveling past the device in such a manner as to enable the camera (10) to take images of each container back-lighted by said flash light flux; and
   to emit the "bottle-scanning" light flux independently of the flash light flux, so as to be perceived by a human eye as being continuous.

2. An inspection device according to claim 1, characterized in that the system for controlling the lighting system (7) has a manual control (12) for adjusting the intensity of the "bottle-scanning" light flux emitted by the lighting system.

3. An inspection device according to claim 2, characterized in that the manual control (12) is a control member mounted on the lighting system or situated remotely from the lighting system.

4. An inspection device according to claim 1, characterized in that the lighting system (7) includes a first series of individual light sources (14) for "flash" light that are distributed regularly over the light-emitting surface and that are suitable for producing light at a wavelength in the range 650 nm to 5000 nm.

5. An inspection device according to claim 4, characterized in that the individual light sources (14) of the first series and the individual light sources (15) of the second series are positioned in alternating manner on at least one support plate (17) extending in a plane.

6. An inspection device according to claim 5, characterized in that the lighting system (7) includes as its light-emitting surface a diffuser (18) placed in front of the support plate (17) for the individual light sources of the first series and for the light sources of the second series.

7. An inspection device according to claim 6, characterized in that the lighting system (7) includes a protective pane (19) placed in front of the diffuser (18).

8. An inspection device according to claim 1, characterized in that the lighting system (7) includes a second series of individual light sources (15) for emitting "bottle-scanning" flux that are distributed regularly over the light-emitting surface and that are suitable for producing visible light at wavelengths lying in the range 300 nm to 650 nm.

9. An inspection device according to claim 1, characterized in that the lighting system (7) for emitting the flash light flux is controlled by a voltage and/or current and/or pulse duration system to operate at a frequency higher than 50 Hz.

10. An inspection device according to claim 1, characterized in that the lighting system (7) for emitting the flash light flux is controlled by a control system serving to synchronize the passage of containers and the emission of flash light flux and the taking of images by the camera (10).

11. An inspection device according to claim 1, characterized in that the lighting system for emitting the bottle-scanning light flux is controlled by a modulator device operating at a frequency higher than 50 Hz so that the light flux is perceived as being continuous by a human eye.

12. An inspection device including a conveyor (5) on which high temperature glass containers (2) leaving a forming machine (3) are placed in order to cause them to travel in succession at a high rate past at least one inspection device (11) according to claim 1, the inspection installation being characterized in that the lighting system (4) for lighting the containers (2) is placed on one side (5*d*) of the conveyor (5), while the camera (10) is placed on the opposite side (5*c*) of the conveyor in a movement zone (Z) for operators.

13. An inspection installation according to claim 12, characterized in that the lighting system (7) is provided with a manual control member (12) for adjusting the intensity of the "bottle-scanning" light flux, the control member being mounted on the lighting system (7) so as to be accessible for an operator located in the movement zone (Z) and being connected to the system for controlling the lighting system (7).

14. An inspection installation according to claim 12, characterized in that the lighting system (7) includes a housing (9) presenting a light-emitting surface (8) on a front face, the housing (9) being fastened to the conveyor (5).

* * * * *